Figure 1:
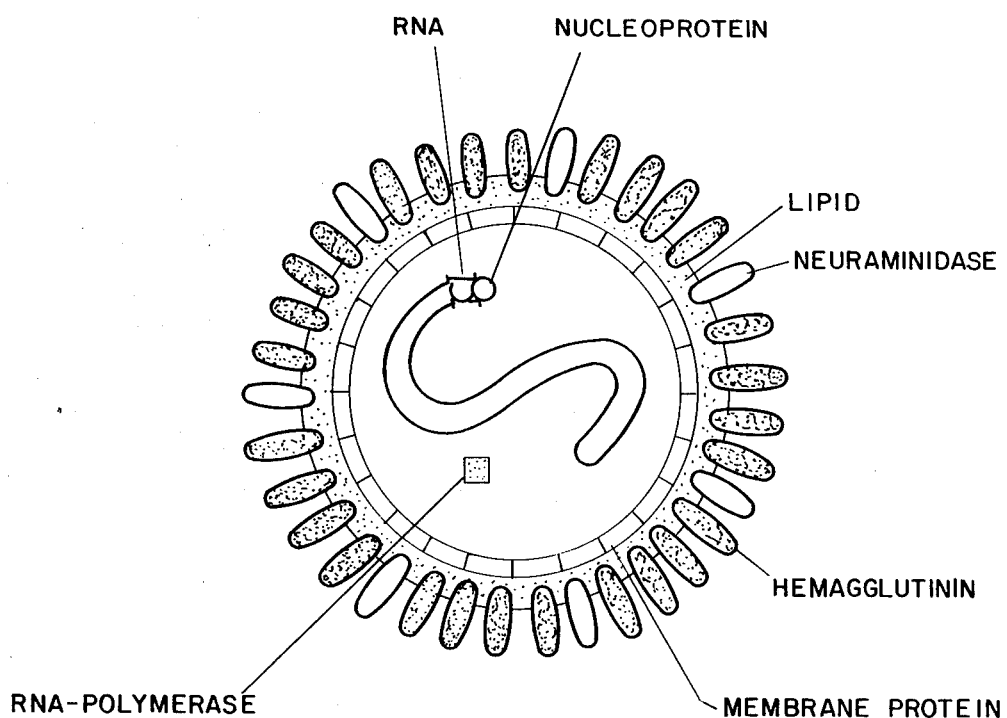

United States Patent [19]

Bachmayer et al.

[11] 4,064,232

[45] Dec. 20, 1977

[54] PROCESS FOR ISOLATING THE IMMUNOGENIC COMPONENTS OF INFLUENZA VIRUSES

[75] Inventors: Helmut Bachmayer, Maria Enzersdorf; Gerhard Schmidt, Modling, both of Austria

[73] Assignee: Sandoz Ltd., Basel, Switzerland

[21] Appl. No.: 687,453

[22] Filed: May 18, 1976

Related U.S. Application Data

[63] Continuation of Ser. No. 539,349, Jan. 8, 1975, abandoned.

[30] Foreign Application Priority Data

Jan. 14, 1974 Switzerland ............................ 447/74

[51] Int. Cl.² .............................................. A61K 39/18

[52] U.S. Cl. ................................................. 424/89
[58] Field of Search ......................................... 424/89

[56] References Cited

PUBLICATIONS

Hayman et al.—FEBS Letters, vol. 29, No. 2, (Jan. 1973), pp. 185–188.
Blough—Virology, vol. 19, (1963), pp. 112–114.
Bucher et al.—Chem. Abst., vol. 77, (1972), p. 71980v.

*Primary Examiner*—Sam Rosen
*Attorney, Agent, or Firm*—Gerald D. Sharkin; Robert S. Honor; Thomas O. McGovern

[57] ABSTRACT

The immunogenic components from influenze viruses are isolated by selectively solubilizing the component in an aqueous media with a cationic detergent.

23 Claims, 1 Drawing Figure

PROCESS FOR ISOLATING THE IMMUNOGENIC COMPONENTS OF INFLUENZA VIRUSES

This is a continuation of application Ser. No. 539,349 filed Jan. 8, 1975 now abandoned.

The present invention relates to influenza vaccines, in particular influenza sub-unit vaccines, and their production by selective solubilisation and isolation of the immunogenic components of influenza virus.

FIG. 1 is a schematic representation of the influenza virus particle. The genetic material, ribonucleic acid (RNA), associated with the group-specific nucleoprotein is surrounded by a double membrane consisting of an inner layer of protein and an outer layer of host-derived lipid material. Two glycoproteins, hemagglutinin and neuraminidase, appear as projections or spikes on the surface of the viral envelope.

It is now well-established that the two glycoproteins, hemagglutinin and neuraminidase, are the major immunogenic components of the influenza virus, all other components, including other virus proteins, nucleic acid and lipids, being non-essential for the induction of immunity. However, the presence of such non-essential materials in an influenza vaccine may lead to undesired side effects and, in any effect, limits the dosage of the vaccine which can be administered and, consequently, the level of immunity which can be achieved.

The ideal influenza vaccine should, therefore, contain the two essential immunogens, hemagglutinin and neuraminidase, in the absence or substantial absence of non-essential components of the viral particle. Previous attempts to separate the influenza immunogens have involved as an initial step, substantially complete disruption or solubilisation of the virus particle, for example with anionic detergents, such as sodium desoxycholate or sodium dodecyl sulphate, such that all or the major portion of the viral components are liberated and go into solution with the immunogens. A subsequent purification or partial purification of the desired immunogens is necessary, and is very elaborate and laborious and the yields are usually low.

The present invention provides a method for isolating the hemagglutinin and neuraminidase immunogens, involving selectively solubilising these components while leaving residual subviral particles consisting of the intact lipid/protein membrane enclosing all other non-essential viral components. The difference in size or density of the solubilised immunogens and the residual sub-viral particles permits ready separation of the immunogens by conventional separating methods utilising such differences in physical properties.

It has thus been found that such selective solubilisation of the hemagglutinin and neuraminidase components can be achieved by treatment of the influenza virus with a cationic detergent.

The present invention accordingly provides a method of isolating the hemgagglutinin and neuraminidase components from influenza virus, comprising treating influenza virus in an aqueous medium with a cationic detergent to selectively solubilise such components, and separating the resulting solubilised such components from residual sub-viral particles.

The method of invention may suitably be applied to influenza Tupe A, A1, A2 or B viruses or mixtures thereof. The particular strain employed will, of course depend on the immunity desired from the immunogens to be isolated but the following may be mentioned as examples: strain A2/Aichi/68, MRC-2 (recombination of Type A2/England/42/72), MRC-11 (recombination of Type A2/Port Chalmers/73), A/Pasteur/30C ("Mutagrip", Institut Pasteur) and B/Mass/67.

The influenza virus to be treated is suitably multiplied in conventional manner, for example by inoculation in 11 day old embryonated chicken eggs, and incubation for a suitable period at a suitable temperature, for example for 2 days at 37° C. The harvested allantoic fluids ae then suitably pooled and the virus suitably concentrated and purified by ultracentrifugation followed by resuspension of the virus in, for example, phosphate buffered physiological saline, or by centrifuging in a continuous flow zonal centrifuge using, for example, a sucrose gradient in phosphate buffered physiological saline, followed by lowering of the sucrose content to, for example, less than 5%, suitably by dialysis against physiological saline, or by Sephadex chromatography or diluting. The concentration of the starting virus is not critical and can be adjusted depending on the desired yield of immunogens.

The pH of the virus concentrate is suitably from 6.5 to 8.5, using buffers, such as phosphate buffer, where required, prior to the addition of the cationic detergent, and the concentrate may also be inactivated, e.g. by the addition of formaldehyde. The cationic detergent is then suitably added to the virus concentrate in the form of an aqueous solution. The appropriate quantity of cationic detergent to be added will depend, for example on the particular detergent employed. However, in general, the cationic detergent is suitably added in such a quantity that the weight ratio of detergent to protein in the resulting mixture is from 1:2 to 1:10, particularly from 1:3 to 1:5. After addition, the mixture is suitably allowed to stnad, for example for a period of 30 minutes to 16 hours at a temperature of, for example 4° C to 37° C, the higher temperatures requiring the shorter standing times. Preferably, the mixture is allowed to stand for 30 to 60 minutes at room temperature, or overnight at 4° C.

The cationic detergent employed may be any cationic detergent sufficiently active to solubilise the hemagglutinin and neuraminidase components, but insufficiently active, under the conditions employed, to disrupt the whole virus particle.

Such cationic detergents may be selected from the well-known class of formula I,

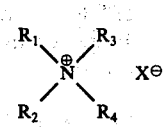

in which $R_4$ signifies alkyl or aryl, $R_1$, $R_2$ and $R_3$ are the same or different and each signifies alkyl or aryl, or $R_1$ and $R_2$, together with the nitrogen atom to which they are attached to form a 5- or 6-membered saturated heterocyclic ring, and $R_3$ signifies alkyl or aryl, or $R_1$, $R_2$ and $R_3$, together with the nitrogen atom to which they are attached, signify a 5- or 6-membered heterocyclic ring, unsaturated at the nitrogen atom, and X signifies an anion.

Representative compounds of formula I include those of formula Ia, $$\begin{array}{c} R_1' \quad \quad CH_3 \\ \diagdown \overset{\oplus}{N} \diagup \\ \diagup \quad \diagdown \\ R_3' \quad \quad R_4' \end{array} \quad X^{\ominus} \qquad \text{Ia}$$

in which
X is as defined above, and
$R_4'$ signifies alkyl of 8 to 22 carbon atoms, and either $R_1'$ and $R_2'$ are the same or different and each signifies methyl or alkyl of 8 to 22 carbon atoms, or
$R_1'$ signifies methyl and $R_2'$ signifies benzyl,
in particular compounds of formula Iaa, $$\begin{array}{c} CH_3 \quad \quad CH_3 \\ \diagdown \overset{\oplus}{N} \diagup \\ \diagup \quad \diagdown \\ CH_3 \quad \quad R_4' \end{array} \quad X^{\ominus} \qquad \text{Iaa}$$

in which
$R_4'$ and X are as defined above, or of formula Iab, $$\begin{array}{c} CH_3 \quad \quad CH_3 \\ \diagdown \overset{\oplus}{N} \diagup \\ \diagup \quad \diagdown \\ C_6H_5CH_2 \quad R_4' \end{array} \quad X^{\ominus} \qquad \text{Iab}$$

in which
$R_4'$ and X are as defined above.

Further representative compounds of formula I are those of formula Ib, $$\left[ \begin{array}{c} \text{pyridinium} - R_4'' \\ | \\ R_5 \end{array} \right] X^{\ominus} \qquad \text{Ib}$$

in which
X is as defined above,
$R_4''$ signifies alkyl of 12 to 18 carbon atoms, and
$R_5$ signifies hydrogen or methyl, preferably hydrogen.

Preferred alkyl radicals of 8 to 22 carbon atoms contain 12 to 18 carbon atoms. Preferred alkyl radicals of 12 to 18 carbon atoms include lauryl, myristyl, cetyl and stearyl.

In the above formulae, X preferably signifies such anions as chloride, bromide, sulphate, or acetate, particularly chloride or bromide.

The preferred compounds of formula Iaa include myristyltrimethylammonium and cetyltrimethylammonium salts, in particular chloride or bromide, more particularly bromides. Preferred compounds of formula Iab include stearyldimethylbenzylammonium salts, in particular chloride or bromide, more particularly bromide. The preferred compounds of formula Ib include cetylpyridinium salts, in particular chloride or bromide, more particularly bromide.

Other cationic detergents which may suitably be employed include benzalkonium chlorides and bromides, for example benzethonium chloride or methylbenzenethonium chloride, as well as such agents as decamethonium chloride.

The preferred cationic detergent for use in the process of the invention is cetyltrimethylammonium bromide.

Upon completion of the process, the hemagglutinin and neuraminidase components may be separated from residual intact sub-viral particles using conventional methods for the separation of materials having different sizes or density, for example by gradient centrifuging, using sucrose or sodium glutamate media, followed by fractionation of the gradients, by sedimentation, by molecular sieve chromatography or by pelleting in an ultracentrifuge.

The mixture of immunogens produced in accordance with the process of the invention are suitable for use in influenza vaccines. For this purpose, the hemagglutinin and neuraminidase components isolated as described above are suitably resuspended in a conventional diluent, for example a physiological isotonic solution, e.g. a 0.9% sodium chloride solution, optionally buffered, e.g. with phosphate buffer. Sucrose remaining from the purification of the initial virus or from the separation of the solubilised components, should suitably be reduced to less than 5% by weight in the vaccine, for example by dialysis. Likewise, the content of cationic detergent remaining should largely be removed, for example reduced to less than 0.01% in the vaccine, for example by dialysis or gel chromatography.

If desired, preserving agents or inactivating agents, such as formaldehyde, may be added to the vaccines, in conventional amounts, for example at a ratio by weight at 1 part to 10,000 parts.

Immunogenicity of the vaccines of the invention may also suitably be improved by inclusion of conventional immunological adjuvants, such as aluminium hydroxide or aluminium phosphate, in conventional amounts, for example, by inclusion of 0.2% of aluminium hydroxide.

As indicated, the vaccines produced in accordance with the invention are useful as vaccines against influenza viruses, for example those mentioned above, as shown, for example, by comparison with whole virus vaccines, having the same immunogenic content, in the mouse protection test. Separate groups of 30 mice are administered, i.p., 0.25 ml of whole virus vaccine and sub-unit vaccine of the invention, each having a hemagglutinin content of about $2^8$. Separate groups are infected, 3,4 and 8 weeks after immunisation, with a virulent virus by spray application. On the ninth day after infection the protection against mortality and against lung lesions is evaluated in each group. The test is repeated using different antigenic contents in the vaccines. The results indicate that the sub-unit vaccines of the invention produce a more prolonged immunity against the infecting virus but otherwise parallel effects to the whole virus vaccine.

For such usage the dosage to be administered will, of course, vary. However, in general, satisfactory results are obtained when administered at a single dose of from about 9 to 43 international units per kg of animal body weight. For the larger mammals, a single dose of from 600 to 3000 internaitonal units is indicated.

The dosage is suitably administered sub-cutaneously or intramuscularly.

The following Examples illustrate the invention.

EXAMPLE 1

Influenza virus of the antigen type X-31 (recombination of the strain $A_2$/Aichi/68) is multiplied in embryonated chicken eggs by incubation at 37° C for two days. The eggs are then chilled at 4° C overnight and the harvested infected allantoic fluid pooled. The virus is subsequently concentrated and purified from the infected allantoic liquid by centrifuging in a continuous flow zonal centrifuge (model RK, Electro-Nucleonics) using a sucrose gradient in phosphate buffered saline. The virus concentrate obtained after reduction of the sucrose content to less than 5% by dialysis against phosphate buffered saline in the cold, has a hemagglutination titre of $1:2^{17}$ and a protein content of 0.7 mg/cc. The immunogens are split off by adding to the virus suspension 1/50 of its volume of an aqueous detergent solution (cetyltrimethylammonium bromide, 1% solution). After 30 to 60 minutes (room temperature) the reaction mixture is worked up by zonal gradient centrifuging using a preformed linear sucrose gradient and subsequent fractionation of the gradients with a peristaltic pump. Hemagglutinin and neuraminidase are solubilized quantitatively and are present in the upper part of the gradient, well separated from the virus residual particle which forms a sediment much more rapidly.

EXAMPLE 2

Multiplication, concentration and cleavage of the virus are effected as described in Example 1. Working up is effected by equilibrium centrifuging in a preformed sucrose gradient. After adjusting equilibrium, the gradient is fractionated and tested: hemagglutinin and neuraminidase are present in the lighter part of the gradient, well separated from the more dense virus residual particle.

EXAMPLE 3

The process is effected as described in Example 1 or 2, except that influenza strain MRC-2 (recombination of type $A_2$/England/42/72) or MRC-11 (recombination of type $A_2$/Port Chalmers/73) is used.

EXAMPLE 4

The process is effected as described in Example 1 or 3, except that the reaction mixture is worked up by molecular sieve chromatography.

EXAMPLE 5

An aqueous solution (0.5%) of cetylpyridinium bromide is added to influenza virus of the type A/Pasteur/30 C ("Mutagrip", Institut Pasteur) which has been inactivated with formol, up to a final concentration of 0.02 to 0.1%. Working up is effected in a manner analogous to that described in Example 1, 2 or 4.

EXAMPLE 6

The process is effected as described in Example 1, 2, 4 or 5, except that the influenza strain B/Mass/67 is used.

EXAMPLE 7

The process is effected as described in Example 1, 3, 5 or 6, except that the cleavage mixture is worked up by pelleting in an ultra-centrifuge. This may, for example, be effected in a Beckmann L-2-65 B centrifuge (rotor 60 Ti, 35 000 r.p.m., 90 minutes). The solubilzed immunogens are present in the supernatant fraction.

EXAMPLE 8

The procedure of any of Examples 1 to 7 is repeated but employing, in place of the cetyltrimethylammonium bromide solution, a 1% solution of myristyltrimethylammonium bromide, benzethonium chloride, methylbenzethonium chloride, decamethonium chloride or stearyldimethylbenzylammonium bromide. Similar results are obtained.

EXAMPLE 9

An influenza vaccine of the invention may be formulated as follows:

Immunogenic mixture: 700 international units
Thiomerosal: 1 part in 10,000 parts
Phosphate buffer in 0.9% physiological saline: to 0.5 ml.

The immunogenic mixture may be produced in accordance with any one of the preceding Examples, for example that produced in Example 3 from the influenza strain MRC-11 (recombination of type A2/Port Chalmers /73).

What is claimed is:

1. A method of isolating the hemagglutinin and neuramuridase components from influenza virus, comprising treating influenza virus in an aqueous medium with a cationic detergent to selectively solubilise components, and separating the resulting solubilised components from residual sub-viral particles.

2. A method according to claim 1, in which the influenza virus is an influenza Type A, $A_1$, $A_2$ or B virus or a mixture of any two or more thereof.

3. A method according to claim 1, in which the influenza virus is strain A2/Aichi/68, MRC-2 (recombination of Type A2/England/42/72), MRC-11 (recombination of Type A2/Port Chalmers/73), A/Pasteur/30C (Mutagrip), or B/Mass/67.

4. A method according to claim 1, in which the cationic detergent is added to a virus concentrate having a pH of from 6.5 to 8.5.

5. A method according to claim 4, in which the virus concentrate is inactivated with formaldehyde prior to the addition of the cationic detergent.

6. A method according to claim 1, in which the cationic detergent is added in the form of an aqueous solution.

7. A method according to claim 1, in which the cationic detergent is added in such a quantity that the weight ratio of detergent to protein in the resulting mixture is from 1:2 to 1:10.

8. A method according to claim 7, in which the weight ratio is from 1:3 to 1:5.

9. A method according to claim 1, in which, after the addition of the cationic detergent, the resulting mixture is allowed to stand for 30 minutes to 16 hours at 4° C to 37° C.

10. A method according to claim 9, in which the mixture is allowed to stand for 30 to 60 minutes at room temperature.

11. A method according to claim 9, in which the mixture is allowed to stand overnight at 4° C.

12. A method according to claim 1, in which the cationic detergent is a compound of the formula,

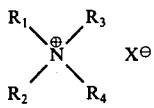

in which
- $R_4$ signifies alkyl or aryl, $R_1$, $R_2$ and $R_3$ are the same or different and each signifies alkyl or aryl, or
- $R_1$ and $R_2$, together with the nitrogen atom to which they are attached form a 5- or 6-membered saturated heterocyclic ring, and $R_3$ signifies alkyl or aryl, or
- $R_1$, $R_2$ and $R_3$, together with the nitrogen atom to which they are attached, signify a 5- or 6-membered heterocyclic ring, unsaturated at the nitrogen atom, and
- X signifies an anion.

13. A method according to claim 1, in which the cationic detergent is a compound of formula,

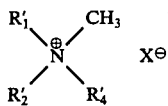

in which
- X is an anion, and
- $R_4'$ signifies alkyl of 8 to 22 carbon atoms, and either $R_1'$ and $R_2'$ are the same or different and each signifies methyl or alkyl of 8 to 22 carbon atoms, or
- $R_1'$ signifies methyl and $R_2'$ signifies benzyl.

14. A method according to claim 1, in which the cationic detergent is a compound of the formula

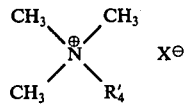

in which $R_4'$ signifies alkyl of 8 to 22 carbon atoms and X is an anion.

15. A method according to claim 1, in which the cationic detergent is a compound of the formula

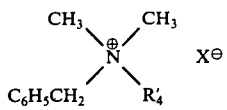

in which $R_4^1$ signifies alkyl of 8 to 22 carbon atoms and X is an anion.

16. A method according to claim 1, in which the cationic detergent is a compound of the formula,

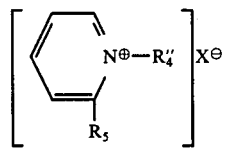

in which
- X is an anion,
- $R_4''$ signifies alkyl of 12 to 18 carbon atoms, and
- $R_5$ signifies hydrogen.

17. A method according to claim 1, in which the cationic detergent is a myristyltrimethylammonium or cetyltrimethylammonium salt.

18. A method according to claim 1, in which the cationic detergent is cetyltrimethylammonium bromide.

19. A method according to claim 1, in which the cationic detergent is a stearyldimethylbenzylammonium salt.

20. A method according to claim 1, in which the cationic detergent is a cetylpyridinium salt.

21. A method according to claim 1, in which the cationic detergent is a benzalkonium chloride or bromide.

22. A method according to claim 1, in which the cationic detergent is benzethonium or methylbenzethonium chloride.

23. A method according to claim 1, in which the cationic detergent is decamethonium chloride.

* * * * *